United States Patent [19]

Teall

[11] Patent Number: 5,554,633
[45] Date of Patent: Sep. 10, 1996

[54] SUBSTITUTED AMINES AS TACHYKININ RECEPTOR ANTAGONISTS

[75] Inventor: Martin R. Teall, Stansted, Great Britain

[73] Assignee: Merck, Sharp & Dohme, Ltd., Hoddesdon, England

[21] Appl. No.: 374,746

[22] Filed: Jan. 27, 1995

[51] Int. Cl.[6] .................... C07D 213/40; C07D 307/52; A61K 31/44; A61K 31/34

[52] U.S. Cl. .................... 514/357; 546/14; 546/159; 546/162; 546/194; 546/245; 546/246; 546/251; 546/255; 548/264.8; 548/370.1; 548/309.7; 548/338.1; 548/374.1; 548/375.1; 548/368.4; 548/307.4; 548/307.1; 548/371.7; 548/306.4; 548/110; 548/127; 548/128; 548/130; 548/131; 548/133; 548/134; 548/135; 548/136; 548/138; 548/194; 548/201; 548/206; 548/217; 548/233; 548/236; 548/245; 548/247; 548/251; 548/253; 548/255; 548/324.5; 548/332.5; 548/267.6; 548/326.5; 548/308.1; 548/334.5; 548/309.4; 548/321.5; 548/335.5; 548/471; 548/333.5; 548/477; 548/557; 548/560; 549/4; 549/69; 549/57; 549/58; 549/77; 549/467; 549/480; 549/493; 514/241; 514/242; 514/245; 514/252; 514/255; 514/256; 514/311; 514/313; 514/352; 514/362; 514/363; 514/364; 514/360; 514/365; 514/370; 514/372; 514/374; 514/378; 514/375; 514/381; 514/383; 514/392; 514/393; 514/399; 514/419; 514/427; 514/406; 514/407; 514/438; 514/443; 514/447; 514/456; 514/471; 544/194; 544/180; 544/182; 544/229; 544/224; 544/242; 544/233; 544/236; 544/322; 544/336

[58] Field of Search ............... 546/14, 335, 159, 546/162, 194, 245, 246, 251, 255, 264.8, 308, 335, 371.4, 375.1; 514/357, 241, 242, 245, 252, 255, 256, 311, 313, 352, 362, 363, 364, 360, 365, 370, 372, 374, 378, 375, 381, 383, 392, 393, 399, 419, 427, 406, 407, 438, 443, 447, 456, 471; 544/194, 180, 182, 229, 224, 242, 233, 236, 322, 336; 548/110, 127, 128, 130, 131, 133, 134, 135, 136, 138, 194, 201, 206, 217, 233, 236, 245, 247, 251, 253, 255, 264.8, 267.6, 308.1, 309, 326, 335.5, 471, 477, 557, 560; 549/4, 69, 57, 58, 77, 467, 480, 493

[56] References Cited

U.S. PATENT DOCUMENTS 5,063,208 11/1991 Rosenberg et al. .................... 514/19

FOREIGN PATENT DOCUMENTS

| 0194464A1 | 9/1986 | European Pat. Off. . |
| 0330940A3 | 9/1989 | European Pat. Off. . |
| 0432442A1 | 6/1991 | European Pat. Off. . |
| 0522808A3 | 1/1993 | European Pat. Off. . |
| 2054588 | 2/1981 | United Kingdom . |

*Primary Examiner*—Zina Northington Davis
*Attorney, Agent, or Firm*—Robert J. North; Melvin Winokur

[57] ABSTRACT

Compounds of formula (I), and salts and prodrugs thereof, wherein Q is optionally substituted phenyl or benzhydryl; X and Y are each H or together form a group=O; Z is O, S or $NR^9$, where $R^9$ is H or $C_{1-6}$alkyl; $R^1$ represents H or $C_{1-6}$alkyl; $R^2$ represents $C_{1-6}$alkyl substituted by $CONR^7(CH_2)_pR^8$ (where $R^7$ is H or $C_{1-6}$alkyl, $R^8$ is optionally substituted heteroaryl and p is 0, 1, 2, 3, 4, 5 or 6); $R^3$ represents H, $C_{1-6}$alkyl or $C_{2-6}$alkynyl; $R^4$ represents H, $C_{1-6}$alkyl or optionally substitute phenyl; $R^5$ represents optionally substituted phenyl; $R^6$ is H or $C_{1-6}$alkyl; and q is 0, 1, 2 or 3; are tachykinin antagonists useful in therapy.

15 Claims, No Drawings

SUBSTITUTED AMINES AS TACHYKININ RECEPTOR ANTAGONISTS

This application is a 35 U.S.C. § 371 application of PCT/GB93/01601, filed Jul. 28, 1993.

This invention relates to a class of compounds, which are useful as tachykinin receptor antagonists.

The tachykinins are a group of naturally-occurring peptides found widely distributed throughout mammalian tissues, both within the central nervous system and in the peripheral nervous and circulatory systems. The structures of three known mammalian tachykinins are as follows:

Substance P:
Arg-Pro-Lys-Pro-Gln-Gln-Phe-Phe-Gly-Leu-Met-$NH_2$
Neurokinin A:
His-Lys-Thr-Asp-Ser-Phe-Val-Gly-Leu-Met-$NH_2$
Neurokinin B:
Asp-Met-His-Asp-Phe-Phe-Val-Gly-Leu-Met-$NH_2$ Evidence for the usefulness of tachykinin receptor antagonists in pain, headache, especially migraine, Alzheimer's disease, multiple sclerosis, attenuation of morphine withdrawal, cardivascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, J. Auton. Pharmacol. (1993) 13, 23–93. Tachykinin antagonists are also believed to be useful in allergic conditions [Hamelet et al Can. J. Pharmacol. Physiol. (1988) 66 1361–7], and immunoregulation [Lotz et al Science (1988) 241 1218–21 and Kimball et al, J. Immunol. (1988) 141 (10) 3564–9]. Tachykinin antagonists may also be useful in the treatment of small cell carcinomas, in particular small cell lung cancer (SCLC) [Langdon et al., Cancer Research (1992) 52, 4554–7].

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythematosis (European patent application no. 0 436 334), conjuctivitis, vernal conjunctivitis, contact dermatitis, atropic dermatitis, urticaria, and other eczematoid dermatitis (European patent application no. 0 394 989) and emesis (European patent application no. 0 533 280).

European patent application no. 0 194 464 discloses compounds of formula (A):

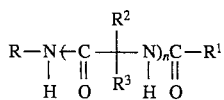
(A)

wherein:
$R^1$ is loweralkyl, arylloweralkyl or optionally substituted phenyl;
$R^2$ is inter alia phenyl;
$R^3$ is inter alia H or loweralkyl;
R is inter alia arylloweralkyl; and
n is inter alia 1.

The compounds are said to have anticonvulsant properties.

Canadian patent application no 2,029,338 discloses compounds of formula (B):

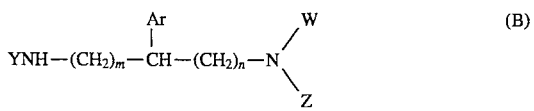
(B)

wherein
Ar is inter alia phenyl;
m is inter alia zero;
Y is h, $RCH_2$ or

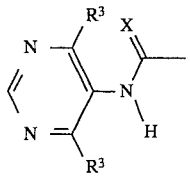

where Ar' is optionally substituted phenyl or naphthyl, R is optionally substituted alkyl, a 5- or 6-membered heterocycle or optionally substituted phenyl, and X is O or S;
n is inter alia 1;
W is inter alia H or $C_{1-20}$alkyl; and
Z is inter alia $R\text{-}CH_2$, where R is inter alia optionally substituted phenyl.

The compounds are said to be ACAT inhibitors useful in lowering blood cholesterol levels.

British patent application no. 2054588 discloses compounds of formula (C):

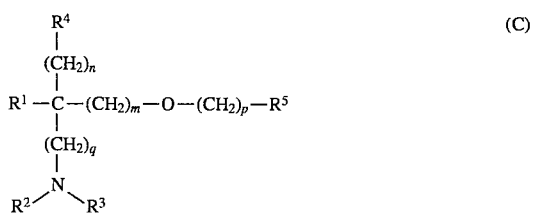
(C)

wherein
$R^1$ is $Cl_{1-10}$ alkyl;
$R^2$ and $R^3$ are H or $Cl_{1-10}$alkyl;
$R^4$ is inter alia optionally substituted phenyl;
$R^5$ is inter alia optionally substituted phenyl;
n is inter alia zero;
m is inter alia 1;
p is inter alia 1; and
q is inter alia zero.

The compounds are said to have anti-spasmolytic, anaesthetic and analgesic activity.

European patent application no. 330 940 discloses compounds of formula (D):

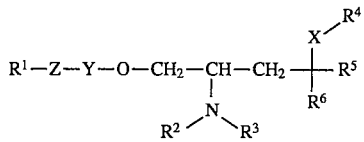

wherein:
R¹ is inter alia an aromatic group;
R² and R³ are Cl$_{1-6}$aliphatic, or together form a ring which may contain further heteroatoms;
R⁴ is an aromatic group;
R⁵ is inter alia an aromatic group;
R⁶ is inter alia H;
X is a bond or CH$_2$;
Y is inter alia C$_{1-6}$hydrocarbyl;
Z is inter alia a bond.

The compounds are said to have anti-depressant effect in mice.

There is no prior art disclosure of the amine substitution of the compounds of the present invention.

The present invention provides a compound of formula (I), or a salt or prodrug thereof:

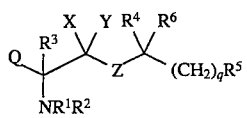

wherein
Q represents optionally substituted phenyl or optionally substituted benzhydryl;
X and Y each represent H or X and Y together form a group=O;
Z represents O, S or NR⁹, where R⁹ represents H or C$_{1-6}$alkyl;
R¹ represents H or C$_{1-6}$alkyl;
R² represents C$_{1-6}$alkyl substituted by CONR⁷(CH$_2$)$_p$R⁸ (where R⁷ is H or C$_{1-6}$alkyl, R⁸ is optionally substituted heteroaryl and p is 0, 1, 2, 3, 4, 5 or 6);
R³ represents H, C$_{1-6}$alkyl or C$_{2-6}$alkyenyl;
R⁴ represents H, C$_{1-6}$alkyl or phenyl (optionally substituted by one or more of C$_{1-6}$alkyl, C$_{2-6}$alkenyl, C$_{2-6}$alkynyl, halo, cyano, nitro, trifluoromethyl, trimethylsilyl, SR$^a$, SOR$^a$, SO$_2$R¹, OR$^a$, NR$^a$R$^b$, NR$^a$COR$^b$, NR$^a$COOR$^b$, COOR$^a$ or CONR$^a$R$^b$, where R$^a$ and R$^b$ each independently represent H, C$_{1-6}$alkyl, phenyl or trifluoromethyl);
R⁵ represents phenyl optionally substituted by one or more of C$_{1-6}$alkyl, C$_{2-6}$alkenyl, C$_{2-6}$alkynyl, halo, cyano, nitro, trifluoromethyl, trimethylsilyl, SR$^a$, SOR$^a$, SO$_2$R$^a$, OR$^a$, NR$^a$R$^b$, NR$^a$COR$^b$, NR$^a$COOR$^b$, COOR$^a$ or CONR$^a$R$^b$, where R$^a$ and R$^b$ are as above defined;
R⁶ represents H or C$_{1-6}$alkyl;
q is 0, 1, 2 or 3.

As used herein, the definition of each expression, when it occurs more than once in any structure, is intended to be independent of its definition elsewhere in the same structure.

The alkyl, alkenyl and alkynyl groups referred to with respect to any of the above formulae may represent straight, branched or cyclic groups or combinations thereof. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkyl-alkyl groups such as cyclopropylmethyl; suitable alkenyl groups include vinyl and allyl; and suitable alkynyl groups include propargyl.

The term "halo" as used herein includes fluoro, chloro, bromo and iodo, especially chloro and fluoro.

Where Q represents substituted phenyl or benzhydryl, suitable substituents include C$_{1-6}$alkyl, C$_{2-6}$alkenyl, C$_{2-6}$alkynyl, halo, cyano, nitro, trifluoromethyl, trimethylsilyl, SR$^a$, SOR$^a$, SO$_2$R$^a$, OR$^a$, NR$^a$R$^b$, NR$^a$COR$^b$, NR$^a$COOR$^b$, COOR$^a$ or CONR$^a$R$^b$, where R$^a$ and R$^b$ are as above defined. One or more substituents may be present and each may be located at any available ring position.

A subgroup of compounds of the present invention is represented by compound of formula (IA), and salts and prodrugs thereof:

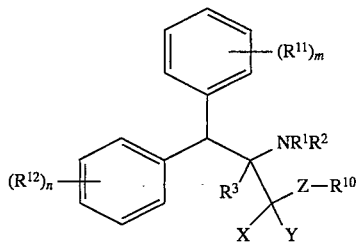

wherein R¹, R², R³, X, Y and Z are as defined for formula (I);
R¹⁰ represents C$_{1-3}$alkyl substituted by a phenyl group which may itself optionally be substituted by one or more of C$_{1-6}$alkyl, C$_{2-6}$alkenyl, C$_{2-6}$alkynyl, halo, cyano, nitro, trifluoromethyl, trimethylsilyl, SR$^a$, SOR$^a$, SO$_2$R$^a$, OR$^a$, NR$^a$R$^b$, NR$^a$COR$^b$, NR$^a$COOR$^b$, COOR$^a$ and CONR$^a$R$^b$, where R$^a$ and R$^b$ are as previously defined;
each R¹¹ independently represents C$_{1-6}$alkyl, C$_{1-6}$alkoxy, halo or trifluoromethyl;
each R¹² independently represents C$_{1-6}$alkyl, C$_{1-6}$alkoxy, halo or trifluoromethyl; and
n and m each represent 0, 1, 2 or 3.

In the compounds of formula (I) it is preferred that Q is unsubstituted phenyl or unsubstituted benzhydryl, more preferably unsubstituted benzylhydryl.

Preferably X and Y each represents H.

Suitably Z represents O or NH. Preferably Z represents O.

Suitable values for the group R¹ include H, methyl, ethyl, propyl, and cyclopropylmethyl. Preferably R¹ is H or C$_{1-4}$alkyl, for example methyl, ethyl or n-propyl. More preferably R¹ is H or methyl.

Suitable values for the heteroaryl moiety R⁸ include thienyl, furyl, pyrrolyl, pyridyl, pyrazolyl, triazolyl, tetrazolyl, thiazolyl, pyrazinyl, pyrimidinyl, pyridazinyl, triazinyl, oxazolyl, oxadiazolyl, thiadiazolyl, isoxazolyl, quinolyl, isothiazolyl, imidazolyl, benzimidazolyl, benzoxazolyl, benzothiophenyl, benzofuranyl and indolyl, any of which may be substituted. Suitable substituents in the heterocyclic ring include one or more of C$_{1-6}$alkyl, C$_{1-6}$alkoxy, phenyl, oxo, thioxo, halo, trifluoromethyl, NR$^a$R$^b$, NR$^a$COR$^b$, CONR$^a$R$^b$, CO$_2$R$^a$, SR$^a$, SO$_2$R$^a$ and CH$_2$OR$^a$ where R$^a$ and R$^b$ are as previously defined.

Preferably the heteroaryl moiety R⁸ represents a substituted or unsubstituted 5- or 6-membered aromatic heterocycle.

It will be appreciated that, when the heteroaryl moiety R⁸ is substituted by an oxo or thioxo substituent, different tautomeric forms are possible so that the substituent may be represented as =O or —OH, or =S or —SH, respectively. For the avoidance of doubt, all such tautomeric forms are embraced by the present invention.

Suitable values for the C$_{1-6}$alkyl moiety of R² include CH$_2$, CH(CH$_3$) and CH$_2$CH$_2$. Preferably the C$_{1-6}$alkyl moiety of R² is CH$_2$ or CH(CH$_3$), more preferably CH(CH$_3$).

Preferably $R^2$ represents $C_{1-6}$alkyl, more preferably $C_{1-4}$alkyl such as $C_{1-2}$alkyl, for example, $CH_2$ or $CH(CH_3)$, substituted by a group $CONR^7(CH_2)_pR^8$ where $R^7$ is preferably H or methyl and p is preferably 1. For example, $R^2$ may suitably represent:

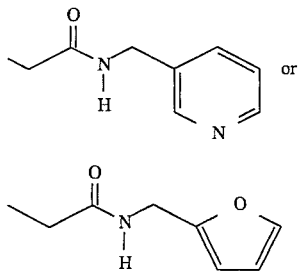

Suitable values for the group $R^3$ include H and methyl, preferably H.

Preferably $R^4$ and $R^6$ each independently represent H or $C_{1-4}$alkyl, especially methyl.

Suitably q is zero, 1 or 2, preferably zero.

Preferably $R^5$ represents substituted phenyl. Suitable phenyl substituents include $C_{1-6}$alkyl such as methyl, ethyl, i-propyl, i-butyl, t-butyl and cyclopropyl, $C_{2-6}$alkenyl such as vinyl, $C_{1-6}$alkoxy such as methoxy, ethoxy and i-propoxy, phenoxy, amino, carboxamido, carbonylmethoxy, trimethylsilyl, nitro, cyano, bromo, chloro, fluoro, iodo and trifluoromethyl. Preferably $R^5$ represents phenyl substituted by one or more groups selected from $C_{1-4}$alkyl, such as methyl and t-butyl, $C_{1-4}$alkoxy, such as methoxy, trifluoromethyl and halo such as bromo, chloro, fluoro and iodo. Preferably $R^5$ represents 3,5-disubstituted phenyl. A particularly preferred value for $R^5$ is 3,5-bistrifluoromethylphenyl.

A preferred sub-group of compounds according to the invention is represented by formula (IB)

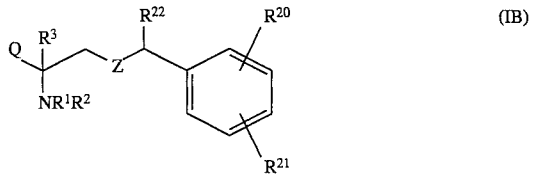

(IB)

wherein Q, $R^1$, $R^2$, $R^3$ and Z are as defined for formula (I) above;

$R^{20}$ represents H, $C_{1-6}$alkyl, $C_{2-6}$alkenyl, $C_{2-6}$alkynyl, halo, cyano, nitro, trifluoromethyl, trimethylsilyl $SR^a$, $SOR^a$, $SO_2R^a$, $OR^a$, $NR^aR^b$, $NR^aCOR^b$, $NR^aCOOR^b$, $COOR^a$ or $CONR^aR^b$, where $R^a$ and $R^b$ are as above defined;

$R^{21}$ represents $C_{1-6}$alkyl, $C_{2-6}$alkenyl, $C_{2-6}$alkynyl, halo, cyano, trifluoromethyl or $OR^a$;

$R^{22}$ represents H or methyl; and salts and prodrugs thereof.

Particularly preferred are compounds of formula (IB) wherein $R^{20}$ is other than H and $R^{20}$ and $R^{21}$ are located in the 3- and 5-positions. Most preferably $R^{20}$ and $R^{21}$ each represent $C_{1-4}$alkyl, $C_{1-4}$alkoxy, halo or trifluoromethyl.

For use in medicine, the salts of the compounds of formula (I) will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, sulphuric acid, oxalic acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Thus, for example, when $R^1$ is other than H, the nitrogen atom to which it is attached may be further substituted to give a quaternary ammonium salt. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The compounds according to the invention may exist both as enantiomers and as diastereomers. It is to be understood that all such isomers and mixtures thereof are encompassed within the scope of the present invention.

The substance P antagonising activity of the compounds described herein was evaluated using the human NK1R assay described in published European patent application no. 0 528 495. The method essentially involves determining the concentration of the test compound required to reduce by 50% the amount of radiolabelled substance P binding to human NK1R, thereby affording an $IC_{50}$ value for the test compound. The compounds of the Examples were found to have $IC_{50}$ values less than 100 nM.

The invention also provides pharmaceutical compositions comprising one or more compounds of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or topical administration including administration by inhalation or insufflation.

The invention further provides a process for the preparation of a pharmaceutical composition comprising a compound of formula (I), or a salt or prodrug thereof, and a pharmaceutically acceptable carrier, which process comprises bringing a compound of formula (I), or a salt or prodrug thereof into association with a pharmaceutically acceptable carrier.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are adminsitered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

For topical administration, for example as a cream, ointment or lotion, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as multiple sclerosis (MS) and amyotropic lateral sclerosis (ALS; Lou Gehrig's disease) and other neuropathological disorders such as peripheral neuropathy, for example, diabetic or chemotherapy-induced neuropathy, and postherpetic and other neuralgias; small cell carcinoma such as small cell lung cancer; respiratory diseases such as chronic obstructive airways disease, bronchopneumonia, bronchospasm and asthma; inflammatory diseases such as inflammatory bowel disease, irritable bowel syndrome, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like, and proliferative vitreoretinopathy; cutaneous diseases such as contact dermatitis, atropic dermatitis, urticaria, and other eczematoid dermatitis; oedema, such as oedema caused by thermal injury; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; emesis, including acute, delayed and anticipatory emesis, for example, induced by chemotherapy, radiation, toxins, pregnancy, vestibular disorders, surgery, migraine and variations in intercranial pressure; disorders of bladder function such as cystitis and bladder detrusor hyperreflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I). 10 For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor antagonist or tachykinin antagonist which acts at NK-2 receptors. The compound of formula (I) and the bronchodilator may be administered to a patient simultaneously, sequentially or in combination.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg of a compound of formula (I) per day. For example, in the treatment of conditions involving the neurotransmission of pain sensations, a suitable dosage level is about 0.001 to 25 mg/kg per day, preferably about 0.005 to 10 mg/kg per day, and especially about 0,005 to 5 mg/kg per day. The compounds may be administered on a regimen of 1 to 4 times per day, preferably once or twice per day.

The compounds according to the invention may be prepared by reaction of a compound of formula (II)

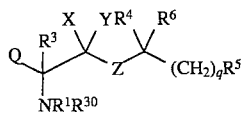

(II)

wherein Q, $R^1$, $R^3$, $R^4$, $R^5$, q, X, Y and Z are as defined for formula (I) and $R^{30}$ represents $C_{1-6}$alkyl substituted by $COOR^{31}$, where $R^{31}$ is H or alkyl with an amine of formula $HNR^7(CH_2)_pR^8$, where $R^7$, $R^8$ and p are as defined for formula (I).

Where $R^{31}$ represents H, the reaction is preferably effected in the presence of a coupling agent, such as 1-(3-dimethylaminopropyl)-3-ethylcarbodiimide.

The reaction is conveniently effected in a suitable organic solvent, such a a halogenated hydrocarbon, for example, dichloromethane.

Where $R^{31}$ represents alkyl, reaction with the amine of formula $HNR^7(CH_2)_pR^8$ is effected at elevated temperature.

Compounds of formula (II) wherein $R^{31}$ is H may be prepared form compounds of formula (II) wherein $R^{31}$ is alkyl, by saponification.

The saponification is conveniently effected using an alkali metal hydroxide, such as, for example, lithium hydroxide.

Compounds of formula (II) wherein $R^{31}$ is alkyl may be prepared from compounds of formula (III)

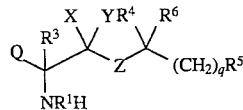

(III)

wherein $R^1$, $R^3$, $R^4$, $R^5$, $R^6$, q, X, Y and Z are as defined for formula (I), by reaction with a compound of formula Hal-$C_{1-6}$alkyl-$COOR^{31}$ wherein Hal represents halo such as chloro, bromo or iodo, and $R^{31}$ represents alkyl, in the presence of a base.

Suitable bases of use in the reaction include alkali metal carbonates such as, for example, potassium carbonate.

Compounds of formula (III) may be prepared as described in published international patent applications nos. WO 93/01160 and WO 93/01165.

Compounds of formula (I) may also be prepared from other compounds of formula (I). Thus, for example, compounds of formula (I) wherein $R^1$ represents H may be reacted with an alkylating agent to produce compounds of formula (I) wherein $R^1$ represents an alkyl group. Suitable procedures are described in the accompanying examples, or will be readily apparent to one skilled in the art.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (-)-di-p-toluoyl-d-tartaric acid and/or (+)-di-p-toluoyl-1-tartaric acid followed by fractional crystallization and regeneration of the free base. The novel compounds may also be resolved by formation of diastereomeric esters or amides, for example, leucine methyl esters, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

EXAMPLE 1

1-((3,5-Bis(trifluoromethyl)phenyl)methyloxy)-3,3-dipheny 1-2-((N-(3-pyridylmethyl)carboxamido)methylammonium) propane bis oxalate salt a) To a solution of diphenylmethyleneiminoacetonitrile (44 g, 0.20 Mol), benzyltrimethyl ammonium chloride (4.4 g, 0.024 Mol) and sodium hydroxide (48.4 g, 1.21 Mol) in toluene ( 40 ml ) and water ( 90ml ) was added bromo-diphenylmethane (149.4 g, 0.60 Mol) at 0° C. After the solution had been stirred at room temperature for 5h a mixture of water (200 ml), ethyl acetate (40 ml) and hexane (160 ml) was added. The solution was filtered and the residue washed with ethyl acetate/hexane and dried in vacuo to give 3.3-diphenyl-2-(diphenylmethyleneimino)proprionitrile 47.6 g. $^1$H NMR (360 MHz, CDCl$_3$) δ7.5–6.87 (20H, m, aryl), 4.8 (1H, d, J=8.85H), 4.69 (1H, d, J=9.2Hz). An analytical sample was recrystallised from ethyl acetate/hexane mp=152°–153° C.

b ) 3,3-Diphenyl-2-(Diphenylmethyleneimino )proprionitrile (Example 1a, 46.7 g, 0.12 Mol) was heated in a solution of 5.5M-hydrochloric acid (200 ml) at reflux for 48h. The solid which crystallized from the cooled solution was removed by filtration, washed with diethyl ether and dried to give $,$-diphenylalanine hydrochloride 21 g. $^1$H NMR (250 MHz, DMSO d$_6$) δ8.6 (3H, vbs), 7.6–7.1 (10H, m), 4.8 (1H, d, J=10.4 Hz), 4.4 (1H, d, J=10.4 Hz).

c) To a solution of 1M-lithium aluminium hydride in diethyl ether (40 ml, 0.04 Mol)was added $,$-diphenylalanine hydrochloride (3.70 g, 0.0133 Mol, Example 1b) over a period of 1h. The solution was heated at reflux for 1h, cooled to room temperature and to the solution was cautiously added 2M-sodium hydroxide (40 ml). After filtering the solution through Celite, the residue was washed with ethyl acetate and the organic phase of the combined tiltrates was washed with water, saturate brine and dried ($MgSO_4$). The solid which formed on removal of the solvent in vacuo was washed with hexane to give 2-amino-3,3-diphenylpropan-1-ol 2.52 g, mp 107°–8° C. $^1H$ NMR (360 MHz, $CDCl_3$) δ7.36–7.14 (10H, m), 3.79 (1H, d, J=10.5 Hz), 3.6 (1H, m), 3.57 (1H, dd, J=10.7Hz and 3.3 Hz), 3.31 (1H, dd, J=10.7 Hz and 6.7 Hz), m/z ($CI^+$) 228 (M+H).

d) A solution of 2-amino-3,3-diphenylpropan-1-ol (2.3 g, 0.010 Mol, Example 1c) and di-t-butyldicarbonate (2.65 g, 0.0122 Mol) in dichloromethane (25 ml) was stirred at room temperature for 1h. The solid which formed on removal of the solvent was recrystallized from diethyl ether to give 2-t-butoxycarbonylamino-3,3-diphenylpropan-1-ol (2.85 g, mp 95°–96° C. $^1H$ NMR (250 MHz, $CDCl_3$) δ7.34–7.15 (10H, m), 4.58 _ (1H, bd), 4.48 (1H, m), 4.1 (1H, d, J=10.6 Hz), 3.67 (1H, dd, J=11.13 Hz and 3.11 Hz), 3.5 (1H, dd, J=11.3 Hz and 4.45 Hz), 1.31 (9H, s).

e) To a solution of the product of Example 1d (8.20 g) and 3,5 bis(trifluoromethyl)benzyl bromide (6.20 ml) in N,N-dimethyl formamide (50 ml) was added sodium hydride (80% suspension in oil, 0.90 g). After stirring the solution for 2 hours, ethyl acetate (250 ml) and water (250 ml) were added, the organic phase washed further with water (10×100 ml), saturated brine (100 ml) and dried ($MgSO_4$) After evaporation the residue was purified by column chromatography on silica gel (eluted with 20–75% ethyl acetate in petroleum ether) to give 1-((3,5-bis(trifluoromethyl)phenyl)methyloxy)-2-(N-t-butoxy carbonylamino)-3,3-diphenylpropane.

f) To the product of Example 1e (42 g), was added a saturated solution of hydrogen chloride in diethyl ether (500 ml), and the resulting solution allowed to stand at room temperature for 48 hr. The precipitated hydrochloride salt was collected by filtration, washed with diethyl ether (100 ml), and dried in vacuo to give 2-ammonium-1-(3,5-bis(trifluoromethyl)phenyl) methyloxy)-3,3-diphenylpropane hydrochloride salt, mp=210° C. (del.); $^1H$ NMR (DMSO $d_6$, 360 MHz) δ3.42 (1H, dd, J=4.7, 10.5 Hz), 3.65 (1H, dd, J=2.6, 10.5 Hz), 4.24 (1H, d, J=11.9 Hz), 4.50 (1H, m), 4.53 (1H, d, J=13 Hz), 4.67 (1H, d, J=13 Hz), 7.18 (1H, m), 7.26 (3H, t, J=7.7 Hz), 7.36 (4H, m), 7.53 (2H, d, J-7.4 Hz), 8.03 (1H, s), 8.05 (2H, s), 8.08 (2H, bs).

g) 2-Amino-1-(3,5-bis(trifluoromethyl)phenyl)methyloxy)-3,3-diphenylpropane (0.365 g, Example 1f, liberated from its hydrochloride salt by partitioning between ethyl acetate and 10% aqueous sodium carbonate solution followed by drying ($MgSO_4$) and evaporation in vacuo), $K_2CO_3$ (0.5 g), and methyl bromacetate (1.23 g) were stirred in dimethyl formamide (5 ml) for 30 minutes. Ethyl acetate (50 ml) and water (50 ml) were added and the organic phase was washed further with water (50 ml), saturated brine (50 ml) and dried ($MgSO_4$). After evaporation the residue was chromatographed on silica gel (eluting with ethyl acetate: hexane (4:6)) to give 1-(3.5-bis(trifluoromethyl)phenyl)methyloxy)-3,3-diphenyl-2-(N -((carbomethoxy)methyl)amino)propane as an oil.

h) To a solution of 1-((3,5-bis (trifluoromethyl)phenyl)methyloxy)-2-(N-((carbomethoxy) methyl)amino)-3,3-diphenylpropane (Example 1g, 2.38 g) in tetrahydrofuran (25 ml) was added 1M-potassium hydroxide solution (25 ml) and the mixture heated to reflux for 16 hours. The solvent was removed by evaporation and 1M-hydrochloric acid was added to an aqueous solution of the residue until pH=2. The gum which formed was recrystallised from aqueous ethanol to give N-(1-((3,5-bis(trifluoromethyl) phenyl)methyloxy)-3,3- diphenylprop-2-yl)glycine mp 116°–119° C.; m/e ($CI^+$) 512 (M+H), ($CI^-$) 511 (M). Found: C, 60.06; H, 4.55; N, 2.66; $C_{26}H_{23}NO_3F_6.0.5(H_2O)$ requires C, 60.00; H, 4.64; N, 2.69%.

i) To a solution of the product of Example 1h (0.350 g), 3-aminomethylpyridine (70 ml), 1-hydroxybenzotriazole (0.092 g) and triethylamine (0.190 ml) in dichloromethane (10 ml) was added 1-(3-dimethylaminopropyl )-3-ethylcarbodiimide ( 0.131 g). After stirring the solution for 16 hours water was added and the organic phase dried ($MgSO_4$). After evaporation in vacuo and column chromatography on silica gel (eluting with 20% to 100% ethyl acetate in petroleum ether) to give 1-((3,5-bis( trifluoromethyl)phenyl)methyloxy)-3,3-diphenyl-2-((N -(3-pyridylmethyl)carboxamido)methylammonium)propane bis oxalate salt, m/e ($CI^+$)= 602 (M+H), ($CI^-$)=600 (M–H). Found: C, 54.54; H, 4.39; N, 5.20; $C_{32}H_{29}N_3O_2F_6.2\times C_2H_2O_4.0.5\times H_2O$ requires C, 54.68; H, 4.33; N, 5.31%.

EXAMPLE 2

1-((3,5-Bis(trifluoromethyl)phenyl)methyloxy)-3,3-dipheny 1-2-((N-(2-furanylmethyl)carboxamido) methylammonium) propane oxalate salt The title compound was prepared from N-(1-((3,5-bis(trifluoromethyl)phenyl)methyloxy)-3,3-diphenylpro p-2-yl)glycine (Example 1h) using an analgous coupling procedure as described in Example 1i. m/e $FAB^+$ 91. Found: C, 57.49; H, 4.53; N, 4.19; $C_{31}H_{28}N_2O_3F_6.(C_2H_2O_4).0.5\times(H_2O)$ requires C, 57,47; H, 4.53; N, 4.06%.

EXAMPLE 3

1-((3,5-Bis(trifluoromethyl)phenyl)methyloxy)-3,3-dipheny 1-2-((N-(2-pyridylmethyl)carboxamido)methylammonium)propan e oxalate salt The title compound was prepared from N-(1-((3,5-bis(trifluoromethyl)phenyl)methyloxy)-3,3-diphenylpro p-2-yl) glycine (Example 1h) using an analogous coupling procedure as described in Example 1i, mp=124°–126° C.; m/e $FAB^+$ 602. Found: C, 55.85; H, 4.40; N, 5.75; $C_{32}H_{29}N_3O_2F_6. 1.75\times(C_2H_2O_4)$ requires C, 56.16; H, 4.31; N, 5.53%.

The following examples illustrate pharmaceutical compositions according to the invention.

EXAMPLE 4A Tablets containing 1–25 mg of compound

|  | Amount mg | | |
| --- | --- | --- | --- |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 4B Tablets containing 26–100 mg of compound

|  | Amount mg | | |
| --- | --- | --- | --- |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 5 Parenteral injection

|  | Amount mg |
| --- | --- |
| Compound of formula (I) | 1 to 100 mg |
| Citric Acid Monohydrat | 0.75 mg |
| Sodium Phosphate | 4.5 mg |
| Sodium Chloride | 9 mg |
| Water for Injections | to 1 ml |

The sodium phosphate, citric acid monohydrate and sodium chloride are dissolved in a portion of the water. The compound of formula (I) is dissolved or suspended in the solution and made up to volume.

EXAMPLE 6 Topical formulation

|  | Amount mg |
| --- | --- |
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

I claim:

1. A compound of formula (I), or a pharmaceutically salt or prodrug thereof:

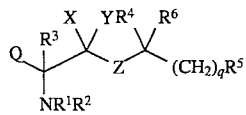

wherein

Q represents optionally substituted phenyl or optionally substituted benzhydryl;

X and Y each represent H or X and Y together form a group =O;

Z represents O, S or $NR^9$, where $R^9$ represents H or $C_{1-6}$alkyl;

$R^1$ represents H or $C_{1-6}$alkyl;

$R^2$ represents $C_{1-6}$alkyl substituted by $CONR^7(CH_2)_pR^8$, where $R^7$ is H or $C_{1-6}$alkyl, R8 is heteroaryl selected from group consisting of substituted or unsubstituted thienyl, furyl, pyrrolyl, pyridyl, pyrazolyl, triazolyl, tetrazolyl, thiazolyl, pyrazinyl, pyrimidinyl, pyridazinyl, triazinyl, oxazolyl, oxadiazolyl, thiadiazolyl, isoxazolyl, quinolyl, isothiazolyl, imidazolyl, benzimidazolyl, benzoxazolyl, benzothiophenyl, benzofuranyl and indolyl, wherein the substituents are selected from the group consisting of $C_{1-6}$alkyl, $C_{1-6}$alkoxy, phenyl, oxo, thioxo, halo, trifluoromethyl, $NR^aR^b$, $NR^aCOR^b$, $CONR^aR^b$, $CO_2R^a$, $SR^a$, $SO_2R^a$, where $R^a$ and $R^b$ each independently represent H, $C_{1-6}$alkyl, phenyl or trifluoromethyl; and p is 0, 1, 2, 3, 4, 5 or 6;

$R^3$ represents H, $C_{1-6}$alkyl or $C_{2-6}$alkyenyl;

$R^4$ represents H, $C_{1-6}$alkyl or phenyl (optionally substituted by one or more of $C_{1-6}$alkyl, $C_{2-6}$alkenyl, $C_{2-6}$alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$ or $CONR^aR^b$, where $R^a$ and $R^b$ each independently represent H, $C_{1-6}$alkyl, phenyl or trifluoromethyl);

$R^5$ represents phenyl optionally substituted by one or more of $C_{1-6}$alkyl, $C_{2-6}$alkenyl, $C_{2-6}$alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$ or $CONR^cR^b$, where $R^a$ and $R^b$ are as above defined;

$R^6$ represents H or $C_{1-6}$alkyl;

q is 0, 1, 2 or 3.

2. A compound as claimed in claim 1 of formula (IA), or a pharamaceutically acceptable salt or prodrug thereof:

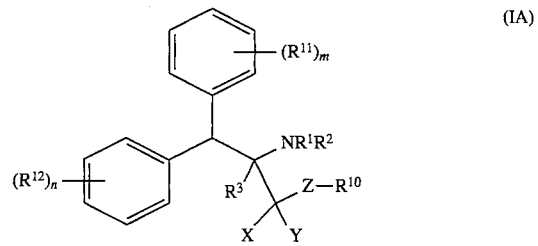

wherein $R^1$, $R^2$, $R^3$, X, Y and Z are as defined for formula (I);

$R^{10}$ represents $C_{1-3}$alkyl substituted by a phenyl group which may itself optionally be substituted by one or more $C_{1-6}$alkyl, $C_{2-6}$alkenyl, $C_{2-6}$alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$ and $CONR^aR^b$, where $R^a$ and $R^b$ are as previously defined;

each $R^{11}$ independently represents $C_{1-6}$alkyl, $C_{1-6}$alkoxy, halo or trifluoromethyl;

each $R^{12}$ independently represents $C_{1-6}$alkyl, $C_{1-6}$alkoxy, halo or trifluoromethyl; and n and m each represent 0, 1, 2 or 3.

3. A compound as claimed in claim 1 wherein Q represents optionally substituted benzhydryl.

4. A compound as claimed in claim 1 wherein $R^5$ represents phenyl substituted by one or more groups selected from $C_{1-4}$alkyl, $C_{1-4}$alkoxy, trifluoromethyl and halo.

5. A compound as claimed in claim 1, wherein $R^4$ and $R^6$ each independently represent H or $C_{1-4}$alkyl.

6. A compound as claimed in claim 1 wherein X and Y each represent H and Z represents O.

7. A compound as claimed in claim 1 selected from:

1-((3,5-bis(trifluoromethyl)phenyl)methyloxy)-3,3-diphenyl-2-((N-(3-pyridylmethyl)carboxamido) methylammonium propane; 1-((3,5-bis(trifluoromethyl)phenyl)methyloxy)-3,3-diphenyl-2-((N-(2-furfurylmethyl)carboxamido) methylammonium propane;

1-((3,5-bis(trifluoromethyl)phenyl)methyloxy)-3,3-diphenyl-2-((N-(2-pyridylmethyl)carboxamido) methylammonium propane;

and pharmaceutically acceptable salts and prodrugs thereof.

8. A pharmaceutical composition comprising a compound as claimed in claim 1 in association with a pharmaceutically acceptable carrier.

9. A process for the preparation of a compound as claimed in claim 1, which process comprises reacting a compound of formula (II):

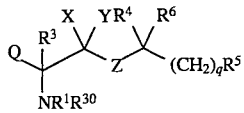

wherein Q, $R^1$, $R^3$, $R^4$, $R^5$, $R^6$, q, X, Y and Z are as defined for formula (I), and $R^{30}$ represents $C_{1-6}$alkyl substituted by $COOR^{31}$, where $R^{31}$ is H or alkyl, with an amine of formula $HNR7(CH_2)_pR^8$.

10. A method for the treatment or prevention of a physiological disorder associated with an excess of tachykinins, which method comprises administration to a patient in need thereof of a tachykinin-reducing amount of a compound according to claim 1.

11. A method according to claim 10 for the treatment or prevention of pain or inflammation.

12. A method according to claim 10 for the treatment or prevention of migraine.

13. A method according to claim 10 for the treatment or prevention of arthritis.

14. A compound according to claim 1 wherein $R^8$ is pyridyl.

15. A compound according to claim 1 wherein p is one.

* * * * *

UNITED STATES PATENT AND TRADEMARK OFFICE
CERTIFICATE OF CORRECTION

PATENT NO. : 5,554,633

DATED : 9/10/96

INVENTOR(S) : Martin R. Teall

It is certified that error appears in the above-identified patent and that said Letters Patent is hereby corrected as shown below:

Title page should list PCT as followings:

[21] Appl. No.: 374,376
[22] PCT Filed: July 28, 1993
[86] PCT No.: PCT/GB93/01601
  § 371 Date: Jan. 27, 1995
  § 102(e) Date: Jan. 27, 1995
[86] PCT Pub. No.: WO 94/03429
  PCT Pub. Date: Feb. 17, 1994

Signed and Sealed this

Twenty-sixth Day of August, 1997

Attest:

BRUCE LEHMAN

Attesting Officer

Commissioner of Patents and Trademarks